United States Patent
Wang et al.

(10) Patent No.: US 11,440,916 B2
(45) Date of Patent: Sep. 13, 2022

(54) SELECTIVE A2A RECEPTOR ANTAGONIST (71) Applicant: InxMed (Nanjing) Co., Ltd., Nanjing (CN)

(72) Inventors: Zaiqi Wang, Beijing (CN); Lihu Yang, Beijing (CN)

(73) Assignee: INXMED (NANJING) CO., LTD., Nanjing (CN)

( * ) Notice: Subject to any disclaimer, the term of this patent is extended or adjusted under 35 U.S.C. 154(b) by 91 days.

(21) Appl. No.: 15/734,986

(22) PCT Filed: Jun. 3, 2019

(86) PCT No.: PCT/CN2019/089773
§ 371 (c)(1),
(2) Date: Dec. 3, 2020

(87) PCT Pub. No.: WO2019/233366
PCT Pub. Date: Dec. 12, 2019

(65) Prior Publication Data
US 2021/0230171 A1 Jul. 29, 2021

(30) Foreign Application Priority Data
Jun. 4, 2018 (CN) .......................... 201810561964.1

(51) Int. Cl.
*C07D 487/14* (2006.01)
*A61K 9/00* (2006.01)

(52) U.S. Cl.
CPC .......... *C07D 487/14* (2013.01); *A61K 9/0053* (2013.01)

(58) Field of Classification Search
CPC .................................................. C07D 487/14
USPC ....................................................... 514/267
See application file for complete search history.

(56) References Cited

U.S. PATENT DOCUMENTS

| | | |
|---|---|---|
| 2002/0099061 A1 | 7/2002 | Neustadt et al. |
| 2004/0023997 A1 | 2/2004 | Neustadt et al. |
| 2004/0116447 A1 | 6/2004 | Gillespie et al. |
| 2015/0157638 A1 | 6/2015 | Michel et al. |
| 2021/0230171 A1 | 7/2021 | Wang et al. |

FOREIGN PATENT DOCUMENTS

| | | |
|---|---|---|
| EP | 3805225 A1 | 4/2021 |
| RU | 2250904 C2 | 4/2005 |
| RU | 2445099 C2 | 3/2012 |
| WO | 9501356 A1 | 1/1995 |
| WO | 0015231 A1 | 3/2000 |
| WO | 2013156614 A1 | 10/2013 |
| WO | 2017189849 A1 | 11/2017 |
| WO | 2018013951 A1 | 1/2018 |
| WO | 2019089773 A1 | 5/2019 |
| WO | 2019233366 A1 | 12/2019 |

OTHER PUBLICATIONS

First Office Action and Search Report for Canadian Patent Application No. 3,102,434, dated Feb. 18, 2022, 4 pages.
First Office Action for Japanese Patent Application No. 2021-517888, dated Feb. 22, 2022, 10 pages.
PCT Patent Application Serial No. PCT/CN2019/089773, English translation of International Search Report, dated Aug. 29, 2019, 5 pages.
Yang et al., "Characterization of the potency, selectivity, and pharmacokinetic profile for six adenosine A2A receptor antagonists," Naunyn-Schmiedeberg's Arch Pharmacol, 2007, 375:133-144.
De Lera Ruiz et al., "Adenosine A2A receptor as a drug discovery target," Journal Medicinal Chemistry, American Chemical Society, May 8, 2014;57(9):3623-50.
First Office Action and Search Report dated Feb. 25, 2020 for counterpart Chinese patent application No. 201810561964.1, 20 pages.
Shah et al., "Biaryl and heteroaryl derivatives of SCH 58261 as potent and selective adenosine A2A receptor antagonists," Bioorganic & Medicinal Chemistry Letters, vol. 18, No. 1415, 4199-4203, May 2008.
Shah et al., "Design, synthesis, and evaluation of fused heterocyclic analogs of SCH 58261 as adenosine A2A receptor antagonists," Bioorganic & Medicinal Chemistry Letters, vol. 18, No. 1414, May 2008.
Waarde et al., "Potential Therapeutic Applications of Adenosine A2A Receptor Ligands and Opportunities for A2A Receptor Imaging," Medicinal Research Reviews, vol. 38, No. 1, Jan. 2017.
P. G. Baraldi et al. "Synthesis of new pyrazolo[4,3-e]1,2,4-triazolo[1,5-c] pyrimidine and 1,2,3-triazolo[4,5-e]1,2,4-triazolo[1,5-c] pyrimidine displaying potent and selective activity as A2a adenosine receptor antagonists" Bioorganic & Medicinal Chemistry Letters, vol. 4, N21, 1994, 2539-2544.

(Continued)

*Primary Examiner* — Taofiq A Solola
(74) *Attorney, Agent, or Firm* — Hoffman Warnick LLC (57) ABSTRACT

The present invention relates to a selective $A_{2A}$ receptor antagonist, and in particular to a selective $A_{2A}$ receptor antagonist of Formula (I), a pharmaceutical composition comprising the antagonist, use of the antagonist in manufacturing a medicament and in treatment of a disease:

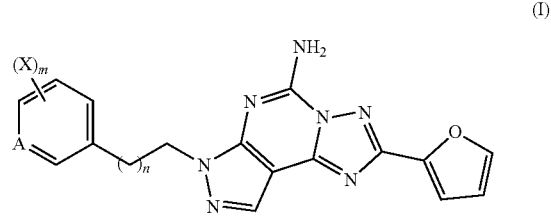

(I)

wherein the groups in Formula (I) are defined as in the specification.

14 Claims, 2 Drawing Sheets

(56) References Cited

OTHER PUBLICATIONS

P. G. Baraldi et al. "7-Substituted 5-amino-2-(2-furyl)pyrazolo[4,3-e]-1,2,4-triazolo[1,5-c]pyrimidines as A2A adenosine receptor antagonists: A study on the importance of modifications at the side chain on the activity and solubility" Journal of Medicinal Chemistry, vol. 45, N1, 2002, 115-126.

P. G. Baraldi et al. "Recent developments in the field of A2A and A3 adenosine receptor antagonists" European Journal of Medicinal Chemistry, vol. 38, 2003, 367-382.

SELECTIVE A2A RECEPTOR ANTAGONIST

TECHNICAL FIELD

Embodiments of the present invention relate to the technical field of small-molecule drugs, and more particularly, to a selective $A_{2A}$ receptor antagonist and its use in treatment of diseases and manufacture of a medicament.

BACKGROUND ART

The adenosine $A_{2A}$ receptor ($A_{2A}$ receptor, or simply $A_{2A}$), one of the four known adenosine receptors $A_1$, $A_{2A}$, $A_{2B}$ and $A_3$, is highly expressed in basal ganglia, the vascular system, spleen, thymus, white blood cells, platelets, coronary arteries and striatum corpora. $A_{2A}$ functions to regulate the myocardial blood flow and increase coronary circulation, and can also suppress immune cells and regulate immune responses. Adenosine, by acting on the $A_{2A}$ receptor, leads to fibrosis of organs such as liver, lung, skin, etc. $A_{2A}$ in the brain plays an influential role in the regulation of glutamate and dopamine release, and thus has become an important target for treatment of diseases like Parkinson's disease. Studies in recent years have also verified the significance of $A_{2A}$ in immunotherapy of tumors, making it an important target for immunotherapy of tumors.

It is believed that $A_{2A}$ receptor antagonists have the potential and capability to treat Parkinson's disease. It is also believed that $A_{2A}$ receptor antagonists can potentially be used to treat inflammation, cancer, fibrosis, ischemia-reperfusion injury, sickle cell disease, diabetic nephropathy, infectious diseases, cognitive impairment and other central nervous system disorder, and motor behavior related diseases.

As different types of adenosine receptors have different functions, $A_{2A}$ receptor antagonists showing high selectivity for the $A_{2A}$ receptor have a relatively small side effect, and have drawn sustained attention in medical research on diseases such as Parkinson's disease and tumors.

SCH-58261 is a potent, highly selective $A_{2A}$ receptor antagonist in the non-xanthine category. Its selectivity for human $A_{2A}$ is 45 times higher than that for the adenosine $A_1$ receptor, 581 times higher than that for the adenosine $A_{2B}$ receptor, and 16 times higher than that for the adenosine $A_3$ receptor. SCH-58261 also shows high antagonistic activity against human $A_{2A}$ (with a $K_i$ value as low as 4 nM) (see Reference 1: Yang et al., Naunyn-Schmiedeberg's Arch Pharmacol (2007) 375:133-144).

SCH-58261 has the following structure:

Although SCH-58261 shows very good in vitro activity and has been validated for its pharmacological effects in various animal models, SCH-58261 failed to become a medicament in further development mainly because SCH-58261 barely has any bioavailability after orally administered. The pharmacological effect of SCH-58261 is achieved by intraperitoneal injection. Intraperitoneally injected SCH-58261 shows a relatively high plasma concentration, but a very low brain concentration, indicating that SCH-58261 has difficulty entering the brain (Yang et al., 2007, ibid.).

Besides the drawback of almost no absorption after oral administration, SCH-58261 is rapidly eliminated after intravenous injection, with a half-life of only 26.7 minutes in the blood of rats (Yang et al., 2007, ibid.). Despite its potent inhibiting effect and excellent selectivity for the $A_{2A}$ receptor, pharmaceutical applications of SCH-58261 have been limited by the lack of oral bioavailability and the short plasma half-life.

Preladenant (SCH 420814) is a potent, highly \selective $A_{2A}$ receptor antagonist that can be orally administered, having the structure below:

The plasma concentration and bioavailability after oral administration and the half-life after intravenous administration of Preladenant are all significantly better than those of SCH-58261. However, Preladenant needs to be administered at least twice a day, and has failed the phase III clinical trial for treatment of Parkinson's disease (see Reference 2: de Lera Ruiz et al., 2014).

Therefore, there is still an urgent need in the art to develop an $A_{2A}$ receptor antagonist that is highly antagonistic against $A_{2A}$ and highly selective for $A_{2A}$, and has high bioavailability and a long elimination half-life after oral administration.

SUMMARY OF INVENTION

In order to solve the above technical problems, the inventors have discovered a group of selective $A_{2A}$ receptor antagonists which have high bioavailability after oral administration, an extended half-life, and a high blood concentration in liver without penetrating into the brain, thereby not affecting the central nerve. The selective $A_{2A}$ receptor antagonists according to the present invention are useful for treatment of $A_{2A}$ receptor-associated diseases, particularly $A_{2A}$ receptor-mediated non-central nerve system diseases, in particular for immunotherapy of tumors, as immune checkpoint inhibitors used in prevention and treatment of cancer (together with other anti-cancer drugs), and for prevention and treatment of fibrosis of organs such as liver, lung and skin, infections, complications caused by diabetes, and the like.

Meanwhile, the compounds according to the present invention are particularly suitable for treatment of non-central nerve system diseases, especially those related to liver, such as non-alcoholic steatohepatitis (NASH), liver fibrosis, cirrhosis, liver cancer, and metastasis of liver tumors. The relative liver-targeting property of the compounds according to the present invention allows effective prevention and treatment of liver diseases (including liver cancer), while having no effect on the central nervous system and minimizing a systemic effect.

The first aspect of the present invention provides a selective $A_{2A}$ receptor antagonist, a pharmaceutical composition comprising the antagonist, its use in manufacture of a medicament, and a treatment method using the antagonist.

In an embodiment, the selective $A_{2A}$ receptor antagonist is a compound of Formula (I), or a stereoisomer, hydrate, solvate, pharmaceutically acceptable salt, co-crystal or prodrug thereof:

(I)

wherein
n is 0 or 1, preferably 1;
m is 1 or 2, preferably 1;
A is nitrogen or carbon;
X is each independently —$R_1COOR_2$ or tetrazol-5-yl, preferably —$R_1COOR_2$;
$R_1$ is a direct bond or a $C_{1-4}$ alkylene, preferably a direct bond or a $C_{1-2}$ alkylene;
$R_2$ is H or a $C_{1-4}$ alkyl, preferably H or a $C_{1-2}$ alkyl;
with the proviso that when A is nitrogen, X is not attached to A.

In an embodiment of the invention, in Formula (I), n is 1, $R_1$ is a direct bond, and $R_2$ is H, methyl, ethyl or propyl.

In an embodiment of the invention, in Formula (I), n is 1, $R_1$ is a direct bond, and $R_2$ is H, methyl, or ethyl.

In an embodiment of the invention, in Formula (I), n is 1, m is 1, $R_1$ is a direct bond, and $R_2$ is H, methyl, or ethyl.

In an embodiment of the invention, in Formula (I), n is 1, m is 1, $R_1$ is a direct bond, and $R_2$ is H.

According to a preferred embodiment of the invention, in the compound of Formula (I) of any of the above embodiments, X is —$R_1COOR_2$.

According to a preferred embodiment of the invention, in the compound of Formula (I) of any of the above embodiments, X is —COOH.

According to a preferred embodiment of the invention, in the compound of Formula (I) of any of the above embodiments, X is tetrazol-5-yl.

According to a preferred embodiment of the invention, in the compound of Formula (I) of any of the above embodiments, A is carbon.

According to a preferred embodiment of the invention, in the compound of Formula (I) of any of the above embodiments, m=1, and X is at the para position of the phenyl or pyridyl group.

According to a preferred embodiment of the invention, in the compound of Formula (I) of any of the above embodiments, m=1, and X is at the meta position of the phenyl or pyridyl group.

According to a preferred embodiment of the invention, provided are the following compounds, or a stereoisomer, hydrate, solvate, pharmaceutically acceptable salt, co-crystal or prodrug thereof:

-continued

In another embodiment of the present invention, provided is a pharmaceutical composition, comprising: a compound or preferred compound of Formula (I) according to any one of the embodiments described above, or a stereoisomer, hydrate, solvate, pharmaceutically acceptable salt, co-crystal or prodrug thereof; and a pharmaceutically acceptable carrier or excipient. Preferably, the pharmaceutical composition is a pharmaceutical composition for oral administration.

In yet another embodiment of the present invention, provided is a use of a compound or preferred compound of Formula (I) according to any one of the embodiments described above, or a stereoisomer, hydrate, solvate, pharmaceutically acceptable salt, co-crystal or prodrug thereof, in the manufacture of a medicament for treating or preventing tumors, tumor metastasis, organ fibrosis, infections, or complications caused by diabetes. Preferably, the medicament is an oral medicament.

In still another embodiment of the present invention, provided is a method for treating or preventing tumors, tumor metastasis, organ fibrosis, infections, or complications caused by diabetes, the method comprising administering an effective dose of a compound or preferred compound of Formula (I) according to any one of the embodiments described above, or a stereoisomer, hydrate, solvate, pharmaceutically acceptable salt, co-crystal or prodrug thereof, to a subject in need thereof. Preferably, the administering is by oral administration.

In the above embodiments, the organ fibrosis is preferably the fibrosis of liver, kidney, pancreas, skin or lung; the medicament is preferably an oral medicament and/or an immunotherapeutic medicament against tumors; the tumor is preferably melanoma; and the tumor metastasis is preferably metastasis of melanoma.

The second aspect of the present invention provides a method for increasing oral bioavailability of SCH-58261 and/or prolonging the half-life of SCH-58261.

In an embodiment, the method comprises introducing 1 to 5 substituents X onto the benzene ring of the molecule of SCH-58261, the substituent(s) X being independently selected from —$R_1COOR_2$ or tetrazol-5-yl, preferably being —$R_1COOR_2$; wherein $R_1$ is a direct bond or a $C_{1-4}$ alkylene, preferably a direct bond or a $C_{1-2}$ alkylene; and $R_2$ is H or a $C_{1-4}$ alkyl, preferably H or a $C_{1-2}$ alkyl.

According to a preferred embodiment of the above method, the substituent X is —COOH, —$COOCH_3$ or —$COOC_2H_5$.

According to a preferred embodiment of the above method, the number of the substituent X is 1 or 2, preferably 1.

According to a preferred embodiment of the above method, the number of the substituent X is 1, and the substituent X is —COOH at the para or meta position of the benzene ring, preferably at the para position of the benzene ring.

The third aspect of the present invention provides a method for producing an $A_{2A}$ receptor antagonist for oral administration.

In an embodiment, the method comprises introducing 1 or 2 substituents X onto the benzene ring of the molecule of SCH-58261, the substituent(s) X being independently selected from —$R_1COOR_2$ or tetrazol-5-yl, preferably being —$R_1COOR_2$; wherein $R_1$ is a direct bond or a $C_{1-4}$ alkylene, preferably a direct bond or a $C_{1-2}$ alkylene; and $R_2$ is H or a $C_{1-4}$ alkyl, preferably H or a $C_{1-2}$ alkyl.

According to a preferred embodiment of the above method, the substituent X is —COOH, —$COOCH_3$ or —$COOC_2H_5$.

According to a preferred embodiment of the above method, the number of the substituent X is 1.

According to a preferred embodiment of the above method, the number of the substituent X is 1, and the substituent X is —COOH at the para or meta position of the benzene ring, preferably at the para position of the benzene ring.

DETAILED DESCRIPTION OF INVENTION

I. Definitions

Unless otherwise indicated, the terms used throughout the specification and claims have the following meanings.

All of the carbon, hydrogen, oxygen, or nitrogen involved in the groups and compounds according to the present invention include their isotopes. All of the carbon, hydrogen, oxygen, or nitrogen involved in the groups and compounds according to the present invention are optionally further replaced by one or more of their corresponding isotopes, wherein the carbon isotopes include $^{12}C$, $^{13}C$ and $^{14}C$, the hydrogen isotopes include protium (H), deuterium (D, also known as heavy hydrogen) and tritium (T, also known as superheavy hydrogen), the oxygen isotopes include $^{16}O$, $^{17}O$ and $^{18}O$, and the nitrogen isotopes include $^{14}N$ and $^{15}N$.

"Alkyl" means a linear or branched mono-valent saturated hydrocarbyl group. Examples of alkyl include, but are not limited to, methyl, ethyl, n-propyl, isopropyl, n-butyl, isobutyl, sec-butyl, tert-butyl, n-pentyl, 2-pentyl, 3-pentyl, 2-methyl-2-butyl, 3-methyl-2-butyl, n-hexyl, n-heptyl, n-octyl, n-nonyl, n-decyl, and the like. Such an alkyl group may be optionally further substituted with 1, 2, 3, 4 or 5 substituents selected from F, Cl, Br, and I.

"Alkylene" means a linear or branched di-valent saturated hydrocarbyl group, including —$(CH_2)_v$—, where v is an integer. Examples of alkylene include, but are not limited to, methylene, ethylene, propylene, butylene, and the like. Such an alkylene group may be optionally further substituted with 1, 2, 3, 4 or 5 substituents selected from F, Cl, Br, and I.

A "cocrystal" refers to a crystal formed by an active pharmaceutical ingredient (API) combined with a cocrystal former (CCF) by hydrogen bonding or other non-covalent bonding, wherein API and CCF are present in a fixed stoichiometric ratio therebetween. A cocrystal is a multi-component crystal, including a binary cocrystal formed by two neutral solids, and a multiple cocrystal formed by a neutral solid and a salt or solvate.

A "stereoisomer" refers to a cis-trans isomer, an enantiomer, or a conformational isomer.

A "pharmaceutical composition" refers to a mixture of one or more compounds according to the present invention or its physiologically/pharmaceutically acceptable salt(s) and other components, in which the other components comprise a physiologically/pharmaceutically acceptable carrier or excipient.

A "carrier" means a vehicle or diluent that does not cause significant stimulation to an organism and does not eliminate the biological activity and characteristics of a given compound.

"Excipient" means an inert substance added into a pharmaceutical composition to further facilitate administration of a compound. Examples thereof include, but are not limited to, calcium carbonate, calcium phosphate, various saccharides, different types of starch, cellulose derivatives (including microcrystalline cellulose), gelatin, vegetable oils, polyethylene glycols, diluents, granulating agents, lubricants, binders and disintegrants.

A "prodrug" means a compound that can be converted under physiological conditions or under the action of a solvent into the biologically active compound according to the present invention. A prodrug according to the present invention may be prepared by modification of functional group(s) of the compound of the present invention. Such a modification can be removed in vivo or by conventional operations, so as to give the parent compound.

An "effective amount" means an amount that causes a physiological or medical response in a tissue, system or subject and is a desirable amount, including the amount of a compound that is, after administered to a subject to be treated, sufficient to prevent occurrence of one or more symptoms of the disease or disorder to be treated or to reduce the symptom(s) to a certain degree.

A "solvate" refers to the compound of the present invention or a salt thereof that further contains a stoichiometric or non-stoichiometric amount of solvent bound via a non-covalent intermolecular force. If the solvent is water, the solvate is hydrate.

"$IC_{50}$" means half maximal inhibitory concentration, the concentration that achieves half of the maximum inhibitory effect.

II. Compounds of the Present Invention—Selective $A_{2A}$ Receptor Antagonists

The selective $A_{2A}$ receptor antagonist according to the present invention is a compound of Formula (I), or a stereoisomer, hydrate, solvate, pharmaceutically acceptable salt, co-crystal or prodrug thereof:

wherein
n is 0 or 1, preferably 1;
m is 1 or 2, preferably 1;
A is nitrogen or carbon;
X is each independently —$R_1COOR_2$ or tetrazol-5-yl, preferably —$R_1COOR_2$;
$R_1$ is a direct bond or a $C_{1-4}$ alkylene, preferably a direct bond or a $C_{1-2}$ alkylene;
$R_2$ is H or a $C_{1-4}$ alkyl, preferably H or a $C_{1-2}$ alkyl;
with the proviso that when A is nitrogen, X is not attached to A.

The compound has excellent oral bioavailability and half-life, shows a liver concentration in liver significantly higher than its plasma concentration, but does not penetrates into the brain to affect the central nerve, thereby having a minimal systemic effect.

In an embodiment, in Formula (I), n is 1, $R_1$ is a direct bond, and $R_2$ is H, methyl, or ethyl.

In an embodiment, in Formula (I), n is 1, m is 1, $R_1$ is a direct bond, and $R_2$ is H, methyl, or ethyl.

In an embodiment of the invention, in Formula (I), n is 1, m is 1, $R_1$ is a direct bond, and $R_2$ is H.

According to a preferred embodiment, in the compound of any of the above embodiments, X is —$R_1COOR_2$.

According to a preferred embodiment, in the compound of any of the above embodiments, X is —COOH.

According to a preferred embodiment, in the compound of any of the above embodiments, X is tetrazol-5-yl.

According to a preferred embodiment, in the compound of any of the above embodiments, A is carbon.

According to a preferred embodiment, in the compound of any of the above embodiments, m=1, and X is at the para position of the phenyl or pyridyl group.

According to a preferred embodiment, in the compound of any of the above embodiments, m=1, and X is at the meta position of the phenyl or pyridyl group.

According to a preferred embodiment, the compound of Formula (I) is one of the following:

-continued

According to a preferred embodiment, the compound of Formula (I) is (Compound HZ10126)    ; or

.

III. Pharmaceutical Composition, Use in Manufacture of Medicaments, and Treatment Method The pharmaceutical composition according to the present invention comprises: (i) a compound of Formula (I) or a particular compound described above, or a stereoisomer, hydrate, solvate, pharmaceutically acceptable salt, co-crystal or prodrug thereof; and (ii) a pharmaceutically acceptable carrier or excipient.

The pharmaceutical composition may be formulated for oral administration, intraperitoneal administration, subcutaneous injection, or intravenous injection. Preferably, the pharmaceutical composition is for oral administration.

According to the characteristics of the selective $A_{2A}$ receptor antagonist according to the present invention, the pharmaceutical composition according to the present invention is useful for treatment or prevention of tumors, tumor metastasis, organ fibrosis, infections, or complications caused by diabetes, including liver cancer or liver tumor metastasis.

Accordingly, in another embodiment of the present invention, provided is a use of a compound or preferred compound of Formula (I) described above, or a stereoisomer, hydrate, solvate, pharmaceutically acceptable salt, co-crystal or prodrug thereof, in the manufacture of a medicament for treating or preventing tumors, tumor metastasis, organ fibrosis, infections, or complications caused by diabetes. Preferably, the medicament is an oral medicament.

In yet another embodiment of the present invention, provided is a method for treating or preventing tumors, tumor metastasis, organ fibrosis, infections, or complications caused by diabetes, comprising administering an effective dose of a compound or preferred compound of Formula (I) according to any one of the embodiments described above, or a stereoisomer, hydrate, solvate, pharmaceutically acceptable salt, co-crystal or prodrug thereof, to a subject in need thereof.

In the above embodiments, the organ fibrosis is preferably the fibrosis of liver, kidney, pancreas, skin or lung; the medicament is preferably an oral medicament and/or an immunotherapeutic medicament against tumors; the tumor is preferably melanoma; and the tumor metastasis is preferably metastasis of melanoma.

In a preferred embodiment of the treatment method, the administration is oral administration.

In a preferred embodiment of the treatment method, the effective dose for oral administration to mice is 0.1 to 10 mg/kg/day, preferably 1 to 5 mg/kg/day, and more preferably 2 to 3 mg/kg/day. A person skilled in the art may calculate the dose for administration to other animals, including human, based on the dose for mice.

In a preferred embodiment of the treatment method, the subject is a mammalian, preferably human.

IV. Method for Increasing Oral Bioavailability of SCH-58261 and/or Prolonging the Half-Life of SCH-58261

The second aspect of the present invention provides a method for increasing oral bioavailability of SCH-58261 and/or prolonging the half-life of SCH-58261.

In an embodiment, the method comprises introducing 1 to 5 substituents X onto the benzene ring of the molecule of SCH-58261, the substituent(s) X being independently selected from —$R_1COOR_2$ or tetrazol-5-yl, preferably being —$R_1COOR_2$; wherein $R_1$ is a direct bond or a $C_{1-4}$ alkylene, preferably a direct bond or a $C_{1-2}$ alkylene; and $R_2$ is H or a $C_{1-4}$ alkyl, preferably H or a $C_{1-2}$ alkyl.

According to a preferred embodiment of the method, the substituent X is —COOH, —COOCH$_3$, or —COOC$_2$H$_5$.

According to a preferred embodiment of the method, the number of the substituent X is 1.

According to a preferred embodiment of the method, the number of the substituent X is 1, and the substituent X is —COOH at the para or meta position of the benzene ring, preferably at the para position of the benzene ring.

V. Method for Producing an $A_{2A}$ Receptor Antagonist for Oral Administration The third aspect of the present invention provides a method for producing an $A_{2A}$ receptor antagonist for oral administration. The $A_{2A}$ receptor antagonist for oral administration is preferably a selective $A_{2A}$ receptor antagonist for oral administration.

In an embodiment, the method comprises introducing 1 or 2 substituents X onto the benzene ring of the molecule of SCH-58261, the substituent(s) X being independently selected from —R$_1$COOR$_2$ or tetrazol-5-yl, preferably being —R$_1$COOR$_2$; wherein R$_1$ is a direct bond or a $C_{1-4}$ alkylene, preferably a direct bond or a $C_{1-2}$ alkylene; and R$_2$ is H or a $C_{1-4}$ alkyl, preferably H or a $C_{1-2}$ alkyl.

According to a preferred embodiment of the method, the substituent X is —COOH, —COOCH$_3$ or —COOC$_2$H$_5$.

According to a preferred embodiment of the method, the number of the substituent X is 1.

According to a preferred embodiment of the method, the number of the substituent X is 1, and the substituent X is —COOH at the para or meta position of the benzene ring, preferably at the para position of the benzene ring.

VI. Effects of the Compound According to the Present Invention

The compounds according to the present invention, particularly those obtained by modifying SCH-58261 by the above method, have significantly increased oral bioavailability and plasma concentration, and a significantly prolonged in vivo half-life, thereby being suitable for oral administration.

Specifically, after introduction of acidic substituent(s) X, especially carboxylic group(s), the modified compound has increased oral bioavailability to 10% or more, while SCH-58261 has barely any oral bioavailability. The modified compound has an in vivo half-life of 3 to 5 hours after oral administration, about 7 to 11 times longer than that of SCH-58261. Furthermore, such a modification significantly elevates the liver concentration which is much higher than its plasma concentration. These modified acidic compounds are not brain-penetrating, and thus do not affect the central nerve.

Hence, the compounds according to the present invention can alter the in vivo drug distribution over important organs, do not enter the brain tissue, and have a significantly increased liver concentration. Accordingly, adverse effects on the central nervous system are reduced or prevented, and a therapy for liver can be implemented with a relatively low or no systemic exposure, resulting in improved safety.

In addition, administration of Compound HZ10126 to mice showed an excellent effect of suppressing tumor metastasis.

EXAMPLES

Example 1. Synthesis of Example Compound HZ10126

1.1 Synthesis of HZ10328

-continued

C₂₁H₁₉N₇O₃
Mol. Wt.: 417.42
HZ 10328

Step s1: Compound 1 (423.7 g) was charged into a reactor under N₂ protection, to which NMP (2.1 L) and CuCN (214 g) were added; the mixture was heated to 200° C. to reflux, stirred for 4 hours at this temperature (products at this stage were analyzed by IPC), and cooled to room temperature; ethyl acetate (2.1 L) and a saturated aqueous solution of NH₄Cl (2.1 L) were added, followed by filtration; the organic layer was separated and washed with saturated NH₄Cl (2.1 L); the aqueous layers were combined and extracted with ethyl acetate, and the organic layers were combined and washed with a saturated aqueous solution of NaCl (1.2 L) and then partitioned; the organic layer was dried over Na₂SO₄ and concentrated, to which 200 ml ethyl acetate and 2 L PE were added, followed by stirring for 30 min, filtration, and drying, to obtain Compound 2 (220 g, yield: 67.9%, IPC retention time: 2.19 min) as a brown solid.

Step s2: Compound 2 (212 g) was charged into a reactor under N₂ protection, to which THF (3 L) and PMHS (269 g) were added, and the mixture was cooled to 0° C.; NaBEt₃H (120.7 g) was added dropwise under stirring at 0° C. to 10° C., and the mixture was warmed to room temperature, stirred for 20 hours (products at this stage were analyzed by IPC), and cooled to 0° C. to 10° C.; 500 ml methanol at 0° C. was added slowly, and a 2 L aqueous solution of saturated NaCl was added, followed by stirring for 15 min and partitioning; the aqueous phase was extracted with 1 L ethyl acetate; the organic layers were combined, dried over Na₂SO₄, concentrated, and purified on a column using PE:ethyl acetate (5:1 and 2:1), to obtain 107 g Compound 3 (IPC retention time: 1.61 min) as a yellow solid.

Step s3: Compound 3 (92 g) was charged into a reactor under N₂ protection, to which ethanol (276 ml) was added, and then an aqueous solution (276 ml) of NaOH (75.1 g) was added slowly at 20° C.; the mixture was heated to 90° C., stirred for 10 hours at this temperature (products at this stage were analyzed by IPC), cooled to room temperature, adjusted to a pH below 3 with HCl, and extracted with ethyl acetate (separately with 500 ml and 300 ml); the organic layers were combined, dried over Na₂SO₄, and concentrated, to obtain Compound 4 as a white solid (120 g, yield: 100%, IPC retention time: 1.3 min).

Steps s4 and s5: Compound 4 (120 g) was charged into a reactor under N₂ protection, to which ethanol (400 ml) was added, and then SOCl₂ (148 g) was added slowly at 60° C.; the mixture was heated to 90° C., stirred for 2-3 hours at this temperature, and concentrated to remove the solvent (products at this stage were analyzed by IPC, and new compound was found at IPC retention time: 2.17 min; the production of Compound 5 was confirmed by LCMS: MS m/z=195); DCM was added, followed by concentration to remove the solvent; DCM was added (4.0 w/v), and SOCl₂ (148 g) was added slowly at 60° C.; the mixture was heated to 60° C., stirred overnight at this temperature (products at this stage were analyzed by IPC, and a new compound was found at IPC retention time: 3.2 min), and cooled to room temperature; a cold aqueous solution of NaHCO₃ (500 ml) was added slowly at 10° C. to adjust the pH to >7; the resultant was extracted with MTBE (500 ml), washed with aqueous NaHCO₃ (300 ml) and aqueous NaCl (300 ml), concentrated to remove the solvent, and purified on a silica gel column (PE/EA=50/1), to obtain colorless oily Compound 6 (105 g, yield: 68.9%; IPC retention time: 3.2 min; MS m/z=213).

Step s6: Compound 7 (80 g) was charged into a reactor under N₂ protection, to which K₂CO₃ (1.75 eq.) and NMP (800 ml) were added, and equimolar Compound 6 was added; the mixture was heated to 150° C., stirred for 5 hours at this temperature (products at this stage were analyzed by IPC, and a new compound was found at IPC retention time: 2.84 min), stirred for another 2 hours at 160° C., and cooled to room temperature; water (1600 ml) was added to the suspension, which was stirred for 1 hour at room temperature, filtered, dried, and purified by preparative HPLC, to obtain about 52 g of HZ10328 (IPC retention time: 2.84 min).

1.2 Synthesis of HZ10126

HZ10328 (23.7 g) was charged into a reactor under N₂ protection, to which methanol (240 ml), THF (240 ml), water (480 ml) and LiOH (23.8 g) were added sequentially, followed by stirring for 16 hours at room temperature; 6N HCl was added to adjust pH to 4-5, followed by stirring for 2 hours at room temperature, to produce a large amount of precipitate which was filtered and washed with water (500 ml); methanol (30 ml) and ethyl acetate (300 ml) were added, followed by stirring for 4 hours at room temperature and filtration; the resultant was washed with ethyl acetate (150 ml), and oven-dried for 16 hours at 40° C., to obtain 44.5 g of the product HZ10126.

IPC retention time: 2.21 min
HPLC retention time: 2.218 min
LC-MS retention time: 2.077 min
MS m/z=390.85 [M+H]+

1.3 Synthesis of HZ10330

HZ10328 (100 mg) was charged into a reactor under N₂ protection, to which THF (2 ml) and LiAlH₄ (5.0 mg) were added sequentially, followed by stirring for 1-3 hours at room temperature; water was added to quench the reaction; the resultant was purified by preparative HPLC to obtain 50 mg of HZ10330.

IPC retention time: 2.16 min.

Example 2. Measurement of Oral Bioavailability

HZ10126 and other test compounds were each administered to mice at a dose of 2 mg/kg, and the bioavailability, AUC, plasma concentration, level of brain penetration (i.e. brain concentration) and liver concentration after the oral administration were measured and shown in Table 1. The measurement methods are well known to a person skilled in the art.

The results show that, as compared to SCH 58261, the example compound HZ10126 and its ester HZ10328 according to the invention, exhibited a significantly increased $AUC_{0 \to t}$ and half-life. Furthermore, example compound HZ10126 exhibited an $AUC_{0 \to t}$, half-life, and plasma concentration after oral administration all significantly higher than those of the known oral $A_{2A}$ receptor antagonist Preladenant; and compound HZ10328 exhibited an $AUC_{0 \to t}$, half-life, and plasma concentration after oral administration slightly higher than or similar to those of Preladenant.

In particular, example compound HZ10126 was highly enriched in liver after orally administered: the liver concentration 1 hour after oral administration was 7 times higher than the plasma concentration, and the liver concentration 6 hours after oral administration was 24 times higher than the plasma concentration; meanwhile, no detectable brain concentration was shown. Therefore, this compound can particularly target liver diseases associated with $A_{2A}$ receptor antagonism.

In addition, as shown in the results for HZ10330, converting the carboxylic group on the example compound HZ10126 into hydroxymethyl (—$CH_2OH$) which is also a polar group does not lead to detectable bioavailability, indicating that the significant bioavailability of the example compound is not merely due to improved polarity and hydrophilicity.

TABLE 1

Bioavailability, brain concentration, liver concentration and plasma concentration of test compounds administered to mice at 2 mg/kg

| ID/Name | Chemical formula | Absolute bioavailability (oral) | $AUC_{0\to\tau}$ (ng/ml * h) | Half-life | Plasma concentration 4 and 6 hours after oral administration (ng/ml) | Brain penetration | Liver concentration/ Plasma concentration |
|---|---|---|---|---|---|---|---|
| HZ10126 |  | 13.4% | 371 ± 62.9 | >4-5 h | 4 h: 52.0 ± 7.03<br>6 h: 28.9 ± 9.79 | No penetration | 1 h post administration: 7;<br>6 h post administration: 24 |
| HZ10136 |  | 0.73% | 7.42 ± 5.66 | <30 min | 2.57 ± 0.10 | No penetration | 1 h post administration: 2.3 |
| HZ10168 |  | | 93.9 ± 40.8 | | 4.50 ± 2.53 | | |
| HZ10330 |  | 0 (not detected at all pharmacokinetic time points) | Not applicable | Not applicable | Not detected from 1 h after oral administration | | Not applicable |

TABLE 1-continued

Bioavailability, brain concentration, liver concentration and plasma concentration of test compounds administered to mice at 2 mg/kg

| ID/Name | Chemical formula | Absolute bioavailability (oral) | AUC$_{0 \to t}$ (ng/ml * h) | Half-life | Plasma concentration 4 and 6 hours after oral administration (ng/ml) | Brain penetration | Liver concentration/ Plasma concentration |
|---|---|---|---|---|---|---|---|
| HZ10328 |  | | 233 ± 73.5 | 3.03 h | 4 h: 24.0 ± 8.02 | | |
| SCH 58261 |  | Basically 0 | Not applicable | *26.7 min [1] | No significant meaningful concentration | | Not applicable |
| Preladenant |  | | 285 ± 113 | 2.1 h [2] | 6 h: 6.20 ± 7.27 | Brain conc.:Plasma conc. = 1:1 [2] | |

*the half-life of SCH 58261 is its half-life after intravenous injection

Example 3. Antagonistic Activity ($IC_{50}$) of Compounds Against $A_{2A}$ Receptor The $IC_{50}$ (nM) values of the example compound HZ10126 and several reference compounds against the rat $A_{2A}$ receptor were measured in an in vitro assay, and the results are shown in Table 2. To be specific, each test compound was added to a 384-well plate Opti-Plate (PerkinElmer, 6007290) at a preset concentration and the wells were sealed with a sealing film. A 20 U $A_{2A}$ membrane (human adenosine $A_{2A}$ receptor membrane, PerkinElmer, $RBH_{A2A}M400UA$) was added to 1 ml Assay Buffer (50 mM Tris-HCl, pH 7.4, 10 mM $MgCl_2$, 1 mM EDTA, 1 μg/ml adenosine deaminase (Diazyme), 4° C.) to a final concentration of 25 nM, of which 50 μl was taken and added to the Opti-plate and incubated at 25° C. for 90 min. 100 μl of a 0.5% PEI solution was added to a UNIFILTER-96 GF/B filter plate (PerkinElmer, 6005177) to soak the filter plate at 4° C. for 90 min, and each well was washed twice with 500 μl Washing Buffer (50 mM Tris-HCl, pH 7.4, 154 mM NaCl). The mixture in the Opti-plate was transferred to the UNIFILTER-96 GF/B filter plate, which was then washed 9 times with Washing Buffer (500 μl/well), and incubated at 55° C. for 10 min. 40 μl ULTIMA GOLD scintillation liquid (PerkinElmer, 77-16061) was added to each well, and the CPM (count per minute) value was read with TopCount (PerkinElmer, NTX). A series of concentrations were established for each compound and the CPM values were plotted versus the concentrations. $IC_{50}$ values were calculated from the curve obtained. The reference compound is $^{(3H)}$-CGS 21680, 250 μCi (30.7 Ci/mM) (PerkinElmer, NET1021).

TABLE 2

Antagonistic activity ($IC_{50}$) of compounds against rat $A_{2A}$ receptor

| ID/Name | Chemical formula | $IC_{50}$ (nM) |
| --- | --- | --- |
| CGS 21680 | | 66.9 |
| HZ10126 | | 1.8 |
| HZ10136 | | 1.1 |
| HZ10168 | | 1.2 |
| Preladenant | | 2.5 |

The results demonstrate that the example compound HZ10126 according to the present invention has potent antagonistic activity against the $A_{2A}$ receptor, which is higher than that of the known oral $A_{2A}$ receptor antagonist Preladenant.

Example 4. Treatment of Tumors

In a mouse model bearing a tumor metastasis, the example compound HZ10126 was orally administered at a dose of 2 mg/kg/day, and produced an excellent inhibitory effect on the tumor.

4.1 Establishment of a Mouse Melanoma Model ($6\times10^4$ Cells/Mouse)

5-week old C58BL/6N mice, half male and half female, were divided into 4 groups, with 10 mice per group. B16-F10 cells were digested and centrifuged, re-suspended in physiological saline and washed once. The cells were counted and adjusted to a cell density of 30×10⁴ cells/ml in a volume of 12 ml. 200 μl of the cell suspension was injected into the tail vain of each mouse (Day 1), and the body weight of mice was recorded once every 3 days. On Day 18, the mice were all sacrificed, lungs were removed, and metastasis tumors were counted and weighed. Livers, kidneys and spleens were taken for HE staining to evaluate the toxicity of the drug. The lungs were subjected to immunohistochemistry and stained for CD11b, F4/80 and CD8.

4.2 Administration

Test drug: HZ10126. 2 mg HZ10126 was dissolved in 80 μl DMSO first, and the resultant solution, while being vortexed, was added dropwise to 10 ml 50% PEG-400 to prepare a 0.2 mg/ml solution.

For the test groups, the HZ10126 solution was intragastrically administered at a dose of 2 mg HZ10126/kg/day. For the control group, an equivalent volume of 50% PGE-400 was administered. From the day of injection of cells, the drug was administered once a day for 18 consecutive days.

4.3 Result

Figure 1:
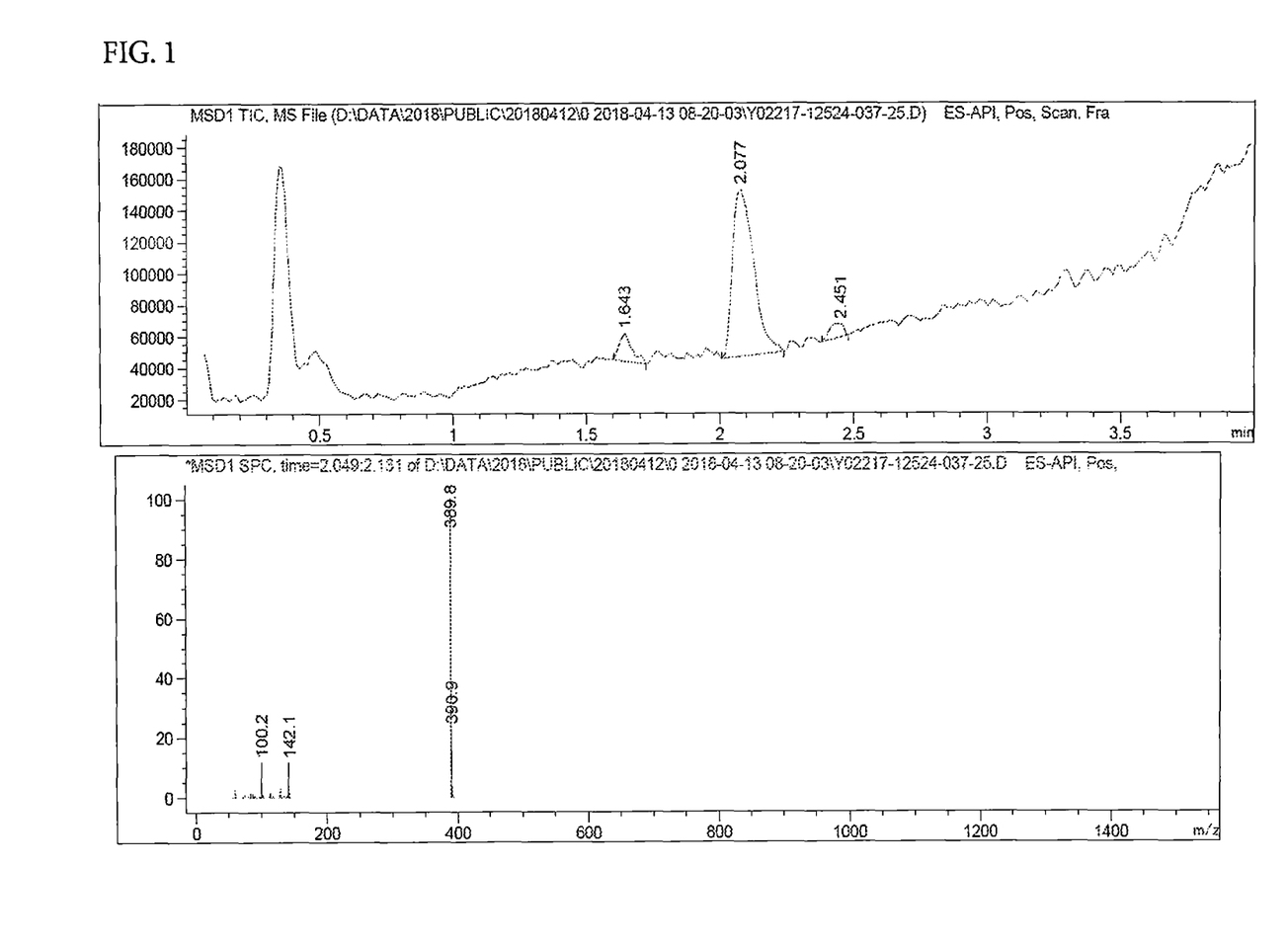
FIG. 1 is an LC-MS chromatogram and a mass spectrum of an example compound HZ10126. In the chromatogram, the peak with a retention time of 2.077 corresponds to HZ10126; and in the mass spectrum, the peak at m/z=390.9 $[M+H]^+$ corresponds to HZ10126.
Figure 2:
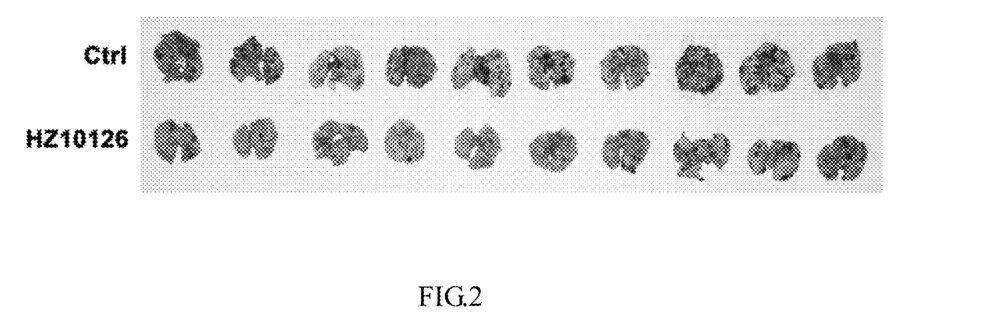
FIG. 2 is photographs of lung metastases of melanoma tumors on Day 18 of the course in which HZ10126 or a solvent control was orally administered to mice once a day.
Figure 3:
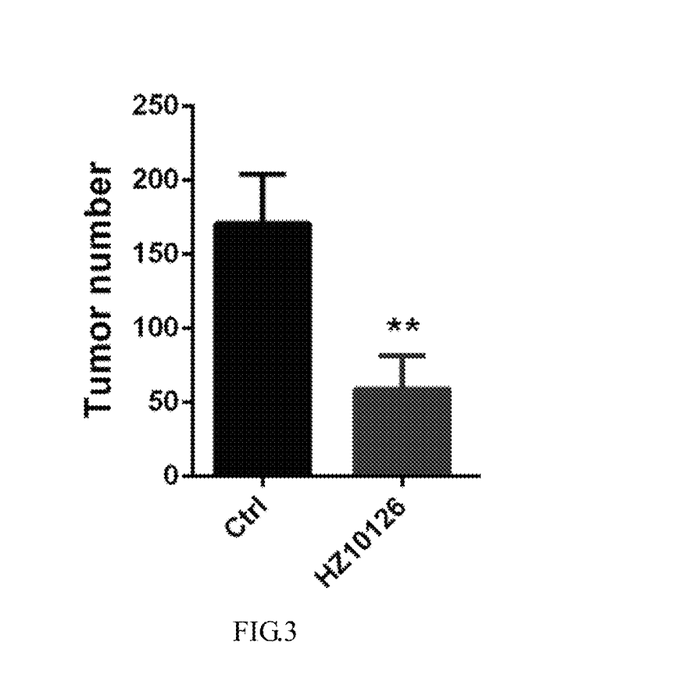
FIG. 3 shows the number of lung metastases of melanoma tumors on Day 18 of the course in which HZ10126 or a solvent control was orally administered to mice once a day.

As a result, on Day 18, the metastases on the lungs in the test groups were obviously less than those in the control group (FIGS. 2 and 3), indicating that HZ10126 can significantly inhibit metastasis of melanoma in mice.

REFERENCES

[1] Yang et al., Characterization of the potency, selectivity, and pharmacokinetic profile for six adenosine $A_{2A}$ receptor antagonists; Naunyn-Schmiedeberg's Arch Pharmacol (2007) 375: 133-144.
[2] de Lera Ruiz M, Lim Y H, Zheng J. (2014) Adenosine $A_{2A}$ receptor as a drug discovery target, J Med Chem. 2014 May 8; 57(9):3623-50.

The invention claimed is:

1. A compound of Formula (I), or a stereoisomer or pharmaceutically acceptable salt thereof:

(I)

wherein
n is 0 or 1,
m is 1 or 2,
A is nitrogen or carbon;
X is each independently —$R_1COOR_2$,
 $R_1$ is a direct bond or a $C_{1-4}$ alkylene,
 $R_2$ is H or a $C_{1-4}$ alkyl,
with the proviso that when A is nitrogen, X is not attached to A.

2. The compound of Formula (I) or a stereoisomer or pharmaceutically acceptable salt thereof according to claim 1, wherein n is 1.

3. The compound of Formula (I) or a stereoisomer or pharmaceutically acceptable salt thereof according to claim 1, wherein $R_1$ is a direct bond; and $R_2$ is selected from the group consisting of H, methyl, ethyl, or propyl.

4. The compound of Formula (I) or a stereoisomer or pharmaceutically acceptable salt thereof according to claim 1, wherein m is 1.

5. The compound of Formula (I) or a stereoisomer or pharmaceutically acceptable salt thereof according to claim 1, wherein A is carbon.

6. The compound of Formula (I) or a stereoisomer or pharmaceutically acceptable salt thereof according to claim 1, wherein the compound of Formula (I) is selected from the group consisting of:

7. A pharmaceutical composition for oral administration, comprising:
 the compound of Formula (I) or a stereoisomer or pharmaceutically acceptable salt thereof according to claim 1; and
 a pharmaceutically acceptable carrier or excipient.

8. The compound of Formula (I) or a stereoisomer or pharmaceutically acceptable salt thereof according to claim 2, wherein $R_1$ is a direct bond; and $R_2$ is selected from the group consisting of H, methyl, ethyl, and propyl.

9. The compound of Formula (I) or a stereoisomer or pharmaceutically acceptable salt thereof according to claim 2, wherein m is 1.

10. The compound of Formula (I) or a stereoisomer or pharmaceutically acceptable salt thereof according to claim 3, wherein m is 1.

11. The compound of Formula (I) or a stereoisomer or pharmaceutically acceptable salt thereof according to claim 4, wherein m is 1.

12. The compound of Formula (I) or a stereoisomer or pharmaceutically acceptable salt thereof according to claim 4, wherein A is carbon.

13. A method for treating a disease associated with the $A_{2A}$ receptor, comprising orally administering an effective amount of the pharmaceutical composition according to claim 7 to a subject in need thereof;
 wherein the disease is selected from the group consisting of tumors, tumor metastasis, organ fibrosis, and infections.

14. The method according to claim 13, wherein the disease is selected from the group consisting of: fibrosis of liver, kidney, pancreas, skin or lung; melanoma; and metastasis of melanoma.

* * * * *